(12) United States Patent
Wolf et al.

(10) Patent No.: US 7,593,107 B2
(45) Date of Patent: Sep. 22, 2009

(54) METHOD AND SYSTEM FOR DIFFUSION ATTENUATED TOTAL REFLECTION BASED CONCENTRATION SENSING

(75) Inventors: James D. Wolf, Kettering, OH (US); Robert E. Kauffman, Centerville, OH (US)

(73) Assignee: Eastman Kodak Company, Rochester, NY (US)

( * ) Notice: Subject to any disclaimer, the term of this patent is extended or adjusted under 35 U.S.C. 154(b) by 527 days.

(21) Appl. No.: 11/395,785

(22) Filed: Mar. 31, 2006

(65) Prior Publication Data
US 2006/0181709 A1    Aug. 17, 2006

Related U.S. Application Data

(63) Continuation-in-part of application No. 10/970,110, filed on Oct. 21, 2004, now Pat. No. 7,375,813.

(51) Int. Cl.
*G01N 21/00* (2006.01)

(52) U.S. Cl. ................... 356/432; 356/124; 356/128; 356/445

(58) Field of Classification Search ......... 356/124–128, 356/432–445
See application file for complete search history.

(56) References Cited

U.S. PATENT DOCUMENTS

| | | |
|---|---|---|
| 3,449,051 A | 6/1969 | Levitt |
| 3,669,545 A | 6/1972 | Gilby |
| 4,382,656 A | 5/1983 | Gilby |
| 4,730,882 A | 3/1988 | Messerschmidt |
| 5,035,504 A * | 7/1991 | Milosevic et al. ........... 356/300 |
| 5,164,589 A | 11/1992 | Sjodin |

(Continued)

FOREIGN PATENT DOCUMENTS

EP    0 284 270    9/1988

(Continued)

OTHER PUBLICATIONS

Refractive Index Sensor With a Guided-Mode Resonant Grating Filter, p. 219—Optical Engineering for Sensing and Nanotechnology (ICOSN 2001), Koichi Iwata, Editor, Proceedings of SPIE vol. 4416 (2001), pp. 219-222.

(Continued)

*Primary Examiner*—L. G Lauchman
*Assistant Examiner*—Iyabo S Alli
(74) *Attorney, Agent, or Firm*—William R. Zimmerli

(57) ABSTRACT

A system for measuring light absorption levels includes a light source providing a light beam and a container for a liquid. The container includes an opening to provide access to the liquid. A prism is disposed over the opening and is operable to direct at least a first portion of the light beam toward the opening to the liquid such that the at least a portion of the first portion of the light beam is reflected back from the liquid forming an attenuated beam. A detector is operable to measure at least one of a portion of the attenuated beam and a second portion of the light beam. The detector is operable to produce at least one of a liquid measurement signal and a reference signal. A device is operable to compute a ratio of the liquid measurement signal to the reference signal to determine a signal ratio.

17 Claims, 10 Drawing Sheets

U.S. PATENT DOCUMENTS

| | | | |
|---|---|---|---|
| 5,170,056 A | | 12/1992 | Berard et al. |
| 5,241,189 A | * | 8/1993 | Vandagriff et al. .......... 356/435 |
| 5,452,083 A | | 9/1995 | Wilks, Jr. |
| 5,572,321 A | | 11/1996 | Pinier et al. |
| 5,835,231 A | | 11/1998 | Pipino |
| 6,067,151 A | | 5/2000 | Salo |
| 6,124,937 A | | 9/2000 | Mittenzwey et al. |
| 6,141,100 A | | 10/2000 | Burka et al. |
| 6,201,607 B1 | | 3/2001 | Roth et al. |
| 6,480,282 B1 | | 11/2002 | Chinowsky et al. |
| 6,504,651 B1 | | 1/2003 | Takatori |
| 6,705,715 B2 | * | 3/2004 | Morita et al. ................. 347/87 |
| 7,221,440 B2 | * | 5/2007 | McCann et al. ............. 356/128 |
| 2002/0149775 A1 | | 10/2002 | Mori et al. |
| 2005/0007596 A1 | | 1/2005 | Wilks, Jr. et al. |
| 2005/0110989 A1 | * | 5/2005 | Schermer et al. ............ 356/445 |

FOREIGN PATENT DOCUMENTS

| | | |
|---|---|---|
| EP | 0 635 714 | 1/1995 |
| EP | 0 714 024 | 5/1996 |
| EP | 0671622 | 12/2000 |
| GB | 2 014 724 | 8/1979 |
| JP | 62 235546 | 10/1987 |
| JP | 2000 065730 | 3/2000 |
| WO | 88/01376 | 2/1988 |
| WO | 93/09421 | 5/1993 |
| WO | 02/077616 | 10/2002 |

OTHER PUBLICATIONS

New Technique for Determining the Optical Constants of Liquids, by C. Dale Keefe and Jason K. Pearson, Society for Applied Spectroscopy, vol. 56, No. 7, 2002-09728.

Absorption Measurement Using a Leaky Waveguide Mode, Optical Review vol. 4, No. 3 (1997) 354-357.

An Optical Fibre Refractometer for Liquids Using Two Measurement Channels to Reject Optical Attenuation, J. Phys. E: Sci. Instrum. 21 (1988) (64-67).

Absorption Sensor Based on Total Internal Reflection Diffraction Grating, Institute of Physics Publishing, J. Opt. A: Pure Appl. Opt. 4 (2002) 382-386.

Design of a Proe for Sensing the Complex Index of Refraction of Liquids, Section 8: Industrial Applications of Sensors pp. 263-268.

Optical Refractometer for Complex Refractive Index Measurement in UV-NIR Range, SPIE vol. 3730, pp. 118-121.

Internal Reflection Spectroscopy by N. J. Harrick, New York, Interscience Publishers [1967].

* cited by examiner

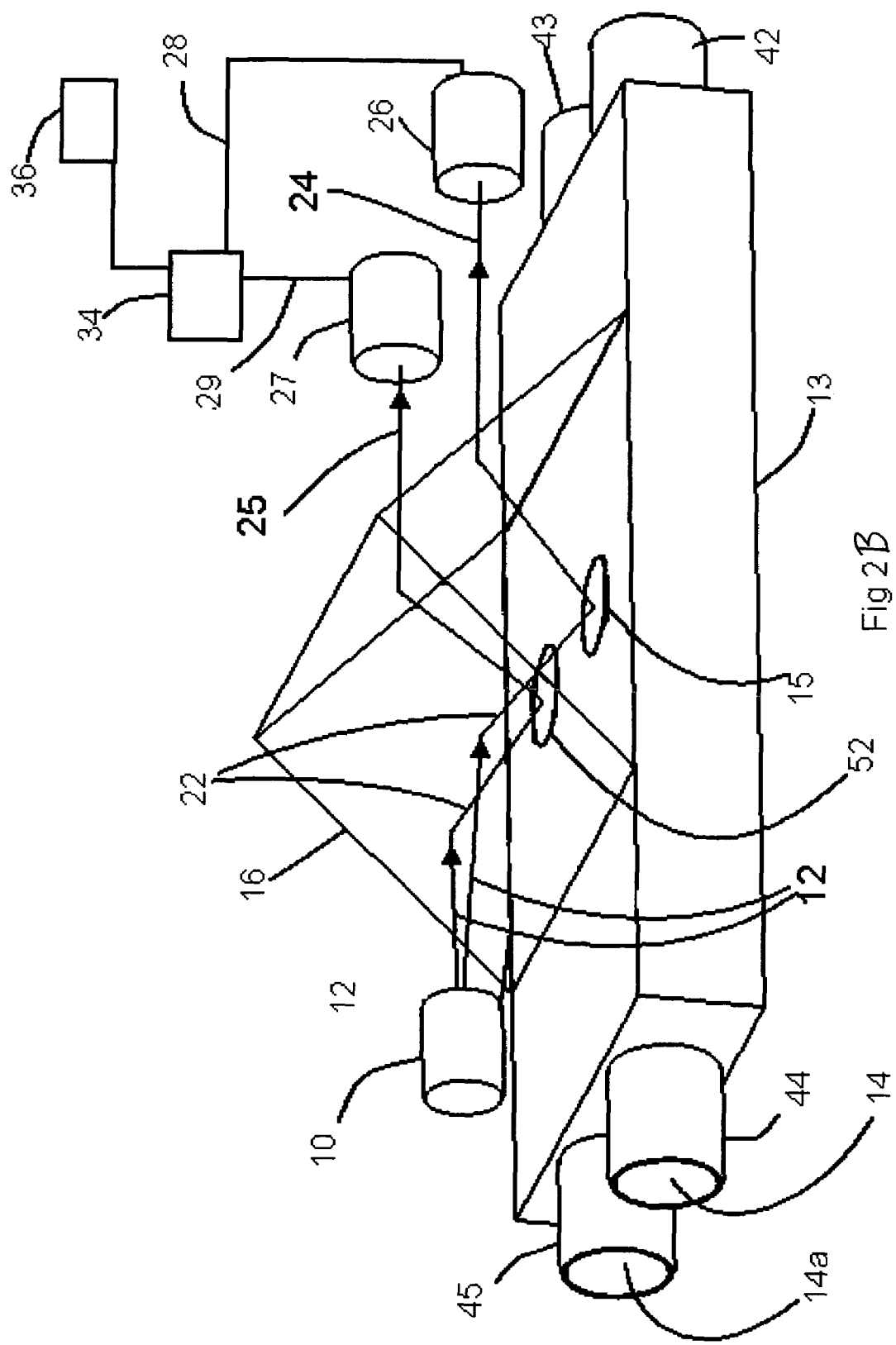

METHOD AND SYSTEM FOR DIFFUSION ATTENUATED TOTAL REFLECTION BASED CONCENTRATION SENSING

CROSS REFERENCE TO RELATED APPLICATIONS

This is a continuation-in-part of application U.S. Ser. No. 10/970,110 filed Oct. 21, 2004 now U.S. Pat. No. 7,375,813.

FIELD OF THE INVENTION

The present embodiments relate to an optical method designed to monitor, on-line or on-site, the dye concentration of black and color inks used by printers or similar printing devices.

BACKGROUND OF THE INVENTION

Attenuated total reflectance techniques used to monitor the dye concentration of in-service printing inks use focusing lens, fiber optics, white light source, gratings to obtain required wavelengths, filters and other expensive, and vibration sensitive optical components. A need exists for a simple, rugged, and inexpensive optical method designed to monitor, on-line or on-site, the dye concentration of black and color inks used by printing presses that is much simpler in concept and much lower in cost than other optical systems currently on the market.

The present embodiments described herein were designed to meet these needs.

SUMMARY OF THE INVENTION

According to one feature of the present invention, a system for measuring light absorption levels for a liquid for use in a ink jet printing system includes a light source operable to provide a light beam and a container adapted to receive a liquid. The container includes an opening to provide access to the liquid. The liquid includes a light absorption level. A prism is disposed over the opening. The prism is operable to direct at least a first portion of the light beam toward the opening to the liquid such that the at least a portion of the first portion of the light beam is reflected back from the liquid forming an attenuated beam. A detector is operable to measure at least one of at least a portion of the attenuated beam and a second portion of the light beam. The detector is operable to produce at least one of a liquid measurement signal that is related to the light absorption level of the liquid from the portion of the attenuated beam and a reference signal from the second portion of the light beam. A device is operable to compute a ratio of the liquid measurement signal to the reference signal to determine a signal ratio with the signal ratio being related to the light absorption level of the liquid.

According to another feature of the present invention, a method of measuring light absorption levels for a liquid for use in a ink jet printing system includes providing a light beam using a light source; providing a container adapted to receive a liquid, the container including an opening to provide access to the liquid, the liquid including a light absorption level; providing a prism disposed over the opening; directing at least a first portion of the light beam using the prism toward the opening to the liquid such that the at least a portion of the first portion of the light beam is reflected back from the liquid; measuring at least one of at least a portion of the attenuated beam and a second portion of the light beam using a detector; producing at least one of a liquid measurement signal that is related to the light absorption level of the liquid from the portion of the attenuated beam and a reference signal from the second portion of the light beam using the detector; and computing a ratio of the liquid measurement signal to the reference signal to determine a signal ratio, wherein the signal ratio is related to the light absorption level of the liquid.

BRIEF DESCRIPTION OF THE DRAWINGS

In the detailed description of the example embodiments presented below, reference is made to the accompanying drawings, in which:

FIG. 2B depicts a schematic perspective view of another example embodiment of the system;

DETAILED DESCRIPTION OF THE INVENTION

Figure 1A:
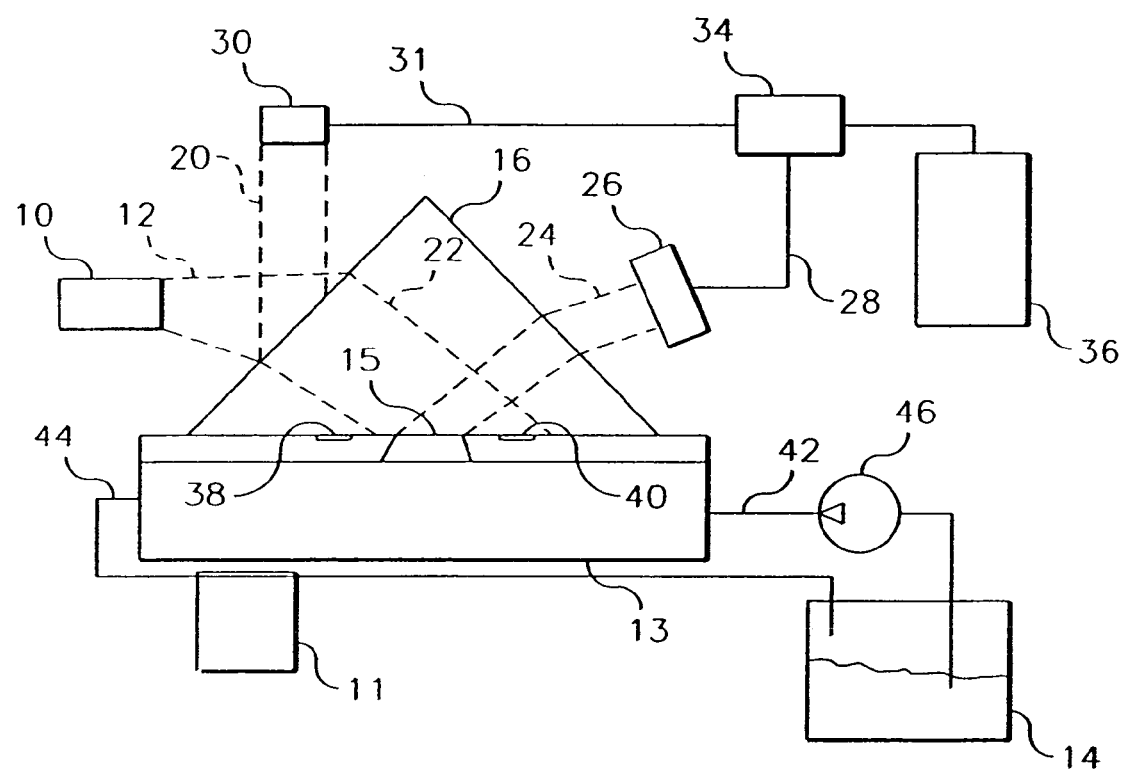
FIG. 1A depicts a schematic cross sectional view of an example embodiment of the system.

Before explaining the present embodiments in detail, it is to be understood that the embodiments are not limited to the particular descriptions and that it can be practiced or carried out in various ways.

The present embodiments include an inexpensive and reliable system to monitor and calculate the light absorption values of fluids, such as liquid inks in a real time, one line continuous basis or as a batch method.

The system embodied herein contain very few parts, which make them less expensive than other systems, such as those with infrared fluorescent markers and readers, and they are easier to maintain, and highly reliable. Additionally, they are easy to incorporate into a manufacturing process for an ink jet printer, as they are small in size. The embodied systems can be easily modified into a portable unit.

Some of the embodied systems and methods use a divergent light beam. The divergent light beam is less expensive to use than other forms of polarized or modified wavelengths. Other embodied systems use non-diverging light beams.

The systems and methods of the invention are not sensitive to the thickness of the fluid flow through the unit, which makes them highly versatile and usable for many different kinds of inks.

These systems and methods provide a predictable and reliable result regardless of fluid flow rates and pressures. Even vibration has little effect on the calculated value with these systems and methods.

The present embodiments can also be used to calculate the ink concentration of two different inks simultaneously using only one container. The benefit of measuring two inks simultaneously makes the embodied systems highly versatile and adaptable for all colors of fluids and all types of inks and easy to use in a printer which has to use sequentially, different types of inks.

The embodied systems and methods can be used as an on-line sensor or can be miniaturized for use as a hand held device for on-site analysis. In contrast to other attenuated total reflectance systems that rely on fiber optics and lenses to focus light beams onto or from a reflective transparent surface, the embodied diffusion attenuated total reflectance system uses a opening formed into a container, wherein the opening is in contact with a glass or quartz prism surface to sample a diverging light beam and to reflect light from that beam. Consequently, the diffusion attenuated total reflectance systems do not have the alignment issues or vibration sensitivity of attenuated total reflectance systems that use fiber optics, lenses to focus the light and gratings to produce specific wavelengths of light.

With reference to the figures, embodiments of a system that measures light absorption levels for liquids in use in a printing system 11 (shown in FIGS. 1A and 1B) are described.

The liquids usable in the system include inks, toners, or colorless liquids. If the liquid is an ink, the ink can be an aqueous-based ink, a polymer-based ink, or a solvent-based ink. An example of a colorless liquid is a cleaning fluid, such as the Kodak Versamark Versapure 1045 Printhead Cleaning Fluid.

The system depicted in FIG. 1A involves a light source 10 adapted to provide a light beam 12. The light beam can be either diverging or non-diverging. The light source is typically a visible light emitting diode (LED). The LED light source can be a red LED, a blue LED, a green LED, an amber LED, or a multi-color LED. The LED preferably emits a wavelength that is a highly absorbing wavelength for colored liquid. Other types of usable light sources include laser diodes, light bulbs, tungsten filaments, or similar light sources. It is desirable that the spectrum of light produced by the light source be stable, not having color shifts with time as such shifts could affect the measured absorption of the liquid.

The system further utilizes a container 13 that is adapted to receive and hold a volume of liquid 14. In a preferred embodiment, the liquid 14 is colorless and is measured for light absorption levels. By measuring the colorless liquid, a base value is created that can be compared to light absorption levels of subsequent fluids that pass through the container.

In an alternative embodiment, the liquid 14 is a colored liquid ink or a toner which has a known colorant concentration. In this embodiment, the known colorant concentration is used as the base value for obtaining a value of what is later referred to as the reference signal. The base value is compared to light absorption levels of subsequent fluids that are passed through the container and measured and a series of computations is performed with this base value to ascertain ink concentration based on total attenuated reflectance of the fluid.

The container 13 in one embodiment has an opening 15 in one surface of the container enabling light from the divergent light beam to impact the liquid. The opening 15 acts as an aperture for light reflected by the fluid from the light beam. When a diverging light beam is used, opening 15 can act as a focusing lens for light reflected by the fluid from the light beam.

The container 13 can be constructed in different variations. FIGS. 2A and 2B depict an embodiment of container 13, wherein the container 13 has two channels for flowing liquid and two openings. In still other embodiments, it is contemplated that the container 13 is simply a box, with only one opening to receive one or more samples of fluid, and a opening or plurality of openings for hand held batch measurement, without the on line design of FIG. 1.

The container 13 is preferably made of a material that is not easily subject to degradation by ultra-violet (UV) light or by chemicals. Preferred materials for the container include stainless steel or Delrin™, a material available from Dupont of Wilmington, Del. The container 13 needs to be made from a material which can be easily machined so that channels and openings can be formed in the container 13 without raw edges. Acetyl resin is another material acceptable for the construction of the container 13.

Continuing with FIG. 1A, the container 13 has an inlet 42 and an outlet 44 for permitting the liquid to enter the container 13 and exit the container 13, respectively. Typically, the flow rate of liquid through the container is contemplated to be between 0.1 liters per minute and 1 liters per minute, but the system can be modified to handle larger flow rates. One or more pumps 46 can be connected to the container 13 to facilitate movement of liquid through the container. A liquid source can engage the pump in order to flow liquid in an uninterrupted and continuous manner through the container 13. The pump 46 can be a liquid pump, such as a gear driven pump from Micropump Corporation.

In an alternative embodiment, the container 13 includes only an inlet 42 and the opening 15. The container 13 can be used for a batch process, wherein the container 13 holds a static, non-flowing volume of liquid that is used to measure the light absorption of the liquid in the container, such as up to 8 liters of fluid. The container could have more than one compartment for measuring two fluids or more in this static or batch method.

In still another embodiment, a non-reflective coating 40 can be added to the container to control and ensure that a non-focused light beam does not come in contact with the measurement detector. Examples of usable coatings include Black Delrin™ and other black, non-flaking non-glossy paints that are stable and do not degrade in the presence of light. Preferably, the coating is only disposed on the surface of the container 13 that is in contact with a prism 16 disposed over the opening 15 which is discussed below.

The prism 16 is disposed over opening 15 to split the light beam into at least a first portion of the light beam 22, for example, a measurement beam 22, and a second portion of the light beam 20, for example, a reference beam 20. The one prism can be place over more than one opening and still used in this method. The prism 16 is typically glass or quartz, but the prism 16 material is not limited to these materials. Usable prisms 16 can be readily obtained from Edmonds Scientific and other high quality glass sources, including Corning Glass of Binghamton, N.Y. Although triangular shaped ninety-degree glass prisms are depicted in the figures, other styles and shapes of prisms can be used. Additionally the prisms can made of different optically clear materials such as sapphire and still used in these embodiments.

The prism 16 is preferably sealed over the opening 15 in a leak tight manner using a seal 38 or sealing material, such as an adhesive sealing material. The seal 38 can be an O-ring, such as elastomeric O-ring; or a gasket, such as EPDM or a terpolymer elastomers made from ethylene propylene diene-monomer or butyl amide gaskets. Alternatively, a clamp can be used to hold the prism 16 over the one or more openings.

A reference detector 30 and a measurement detector 26 are preferably placed beneath the prism 16 and the opening 15. By placing the detectors 26 and 30 beneath the prism 16 and opening 15, the chance of bubbles in the liquid interfering with the measurement detector 26 is reduced when the prism is inverted. The reference detector 30 measures the intensity of the reference beam 20. Known reference detectors are readily available and can be procured though Radio Shack.

A portion of the beam is reflected from the surface of the prism 16 and to the reference detector 30 forming a reference signal 31. The liquid reference signal 31 is used to compensate for the effects of temperature and light source variations-with regard to the intensity of the light source. As a further precaution, a housing (not shown) optionally can be used to enclose completely the entire system, including container, prism, and detectors to protect the device from the elements or dirt in a printing house, or other problems, such as dripping water which could dilute or otherwise effect the sample or the quality of reflected light to be measured.

A portion of the first portion of the light beam 22 passes through the opening 15 to the liquid and is reflected back from the liquid through the opening, forming an attenuated beam. Preferably the first portion of the light beam is incident on the interface between the liquid and the prism at an angle that produces total internal reflection. At such angles, the reflected light is attenuated for light-absorbing liquids. The amount of attenuation is related to the light absorption level of the liquid.

The measurement detector 26 can be any known measurement detector for light, such lights sensors available from Radio Shack. The measurement detector is used to measure the intensity of the attenuated beam to determine a light absorption level of the liquid, which is either the colorless liquid or the colored liquid with the known colorant value. The intensity of the attenuated beam is related to the light absorption level of the liquid. The measurement detector 26 then produces a first liquid measurement signal 28. The measurement detector 26 can be a light sensor that produces a voltage and the voltage can then be measured using a simple voltage measurement device such as a volt meter. The measurement device not only measures the first or colorless liquid value, but then the ink of interest is places in the container and a similar measurement is performed forming a colored liquid measurement signal. Additionally, a colored liquid reference signal is formed in the same manner as the colorless liquid reference signal already described.

Device 34 makes simple mathematical calculations to determine the signal ratio of the liquid based on the four detected values described above. Device 34 can be a logic circuit or a microprocessor, or a PC. The device 34 uses the following formula as the basis for the calculations:

$$SR=LMS/RF$$

Wherein:
SR=Signal Ratio
LMS=Liquid Measurement Signal
RS=Reference Signal

Typically the device 34 can be other than a PC or microprocessor, and PDAs, laptops, even cell phones or calculators can be used as Device 34.

The embodied systems further include software, such as a look-up table or colorant concentration calculation 36, installed on the device 34. The look-up table or colorant concentration calculation 36 is typically constructed by the user of the device by running colorless and colored liquids of known concentrations through the device 34 and recording the signal ratio values into the look-up table or determining the slope of the linear plot produced by plotting the light absorption values of a colorless liquid and of liquid(s) with known colorant concentration(s) versus the colorant concentration of the colored liquids 36. The following formula is used to calculate the light absorption values of the colorless and colored liquids $$LAV=1-SR/SR'$$

Wherein:
LAV=Light Absorption value
SR=Signal ratio of Colored Liquid
SR'=Signal Ratio of Colorless Liquid The embodied systems and methods are utilized to monitor the dye concentration of in-service printing inks using diffusion attenuated total reflectance of the fluids.

The following is an example of one way to use the system. A light from a source, such as a red LED, produces a light beam against the angled surface of the prism which is disposed, over the opening in the container as described above. A portion of the light is reflected by the angled surface and measured by a reference detector. The light measured by the reference detector is used to monitor the output of the light source and the effects of temperature on the detector efficiency. Of the produced light passing through the prism, only the light that comes into contact with the prism surface above the opening in the container is sampled and focused onto the signal detector. A portion of the light, sampled by the opening, is absorbed by the ink filling the opening. The absorbance of the light is inversely proportional to the concentration of the dye in the ink. For example, the detector signal decreases (absorbance increases) as the dye concentration increases. The light detected by the signal detector is compared to the light detected by the reference detector to negate the effects of variations in the light output or detector temperature on the determined dye concentration.

An interchangeable LED can be used in this system. Realignment is not needed when the LED is changed due to malfunction or to a change in the ink color being used in the printer system. For example, a red LED works best for cyan colored inks while a green LED works best for magenta colored inks.

Figure 1B:
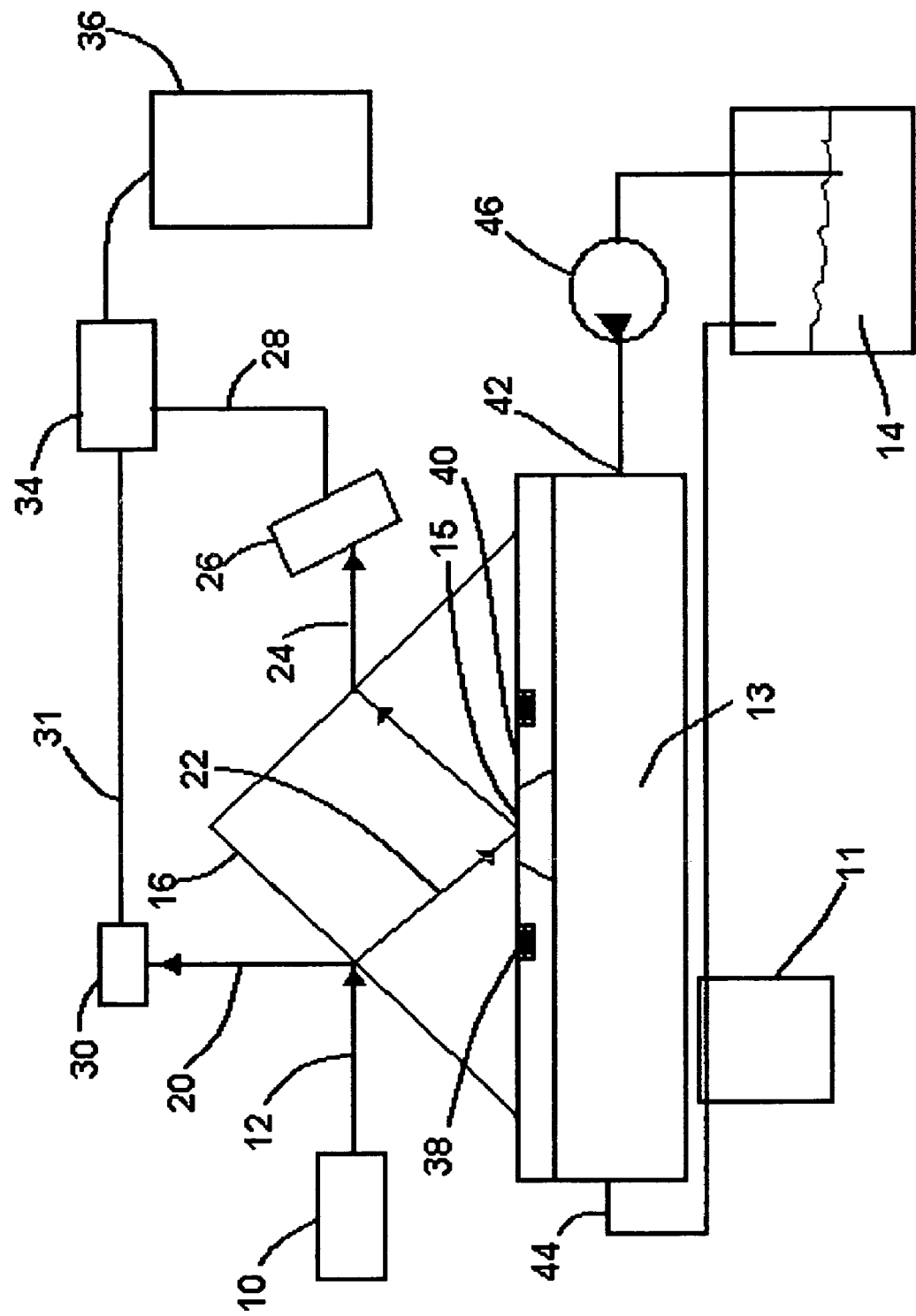
FIG. 1B depicts a schematic cross sectional view of another example embodiment of the system.
Figure 2A:
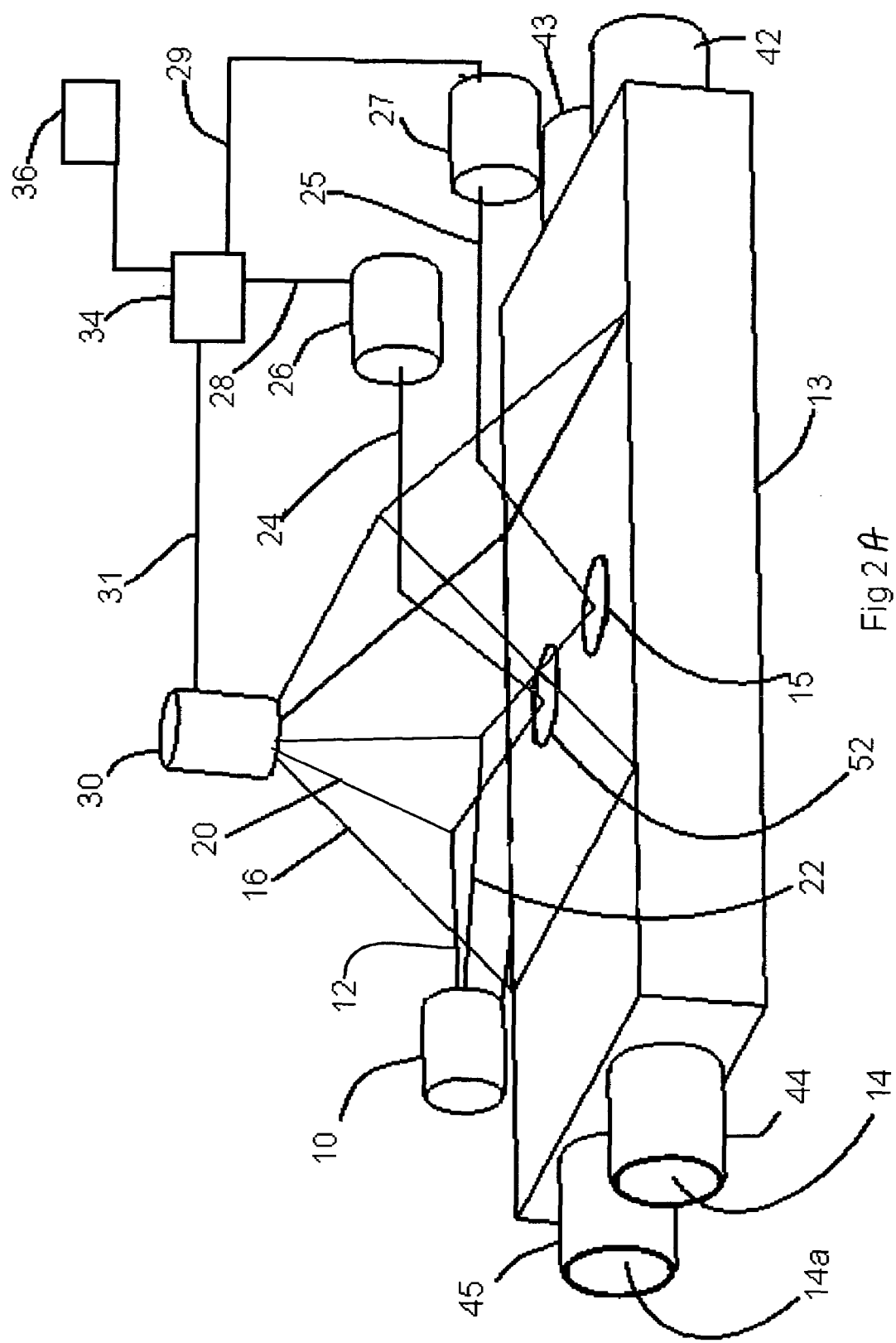
FIG. 2A depicts a schematic perspective view of another example embodiment of the system.

FIG. 1B depicts another example embodiment. The system depicted in FIG. 1B includes a light source 10 adapted to provide a light beam 12. The light source 10 may produce a collimated light beam or a converging light beam. Preferably the light source emits a wavelength that is a highly absorbing wavelength for colored liquid. The light source is typically a visible light emitting diode (LED) or a laser diode. However, other types of usable light sources include light bulbs, tungsten filaments, or similar light sources.

A container 13 includes an opening, for example, a hole, 15 in one surface of the container enabling light from the light beam to impact the liquid. The container 13 has an inlet 42 and an outlet 44 for permitting the liquid to enter the container 13 and exit the container 13, respectively. Typically, the flow rate of liquid through the container is contemplated to be between 0.1 liters per minute and 1 liters per minute, but the system can be modified to handle larger flow rates. One or more pumps 46 can be connected to the container 13 to facilitate movement of liquid 14 through the container. A liquid source can engage the pump in order to flow liquid in an uninterrupted and continuous manner through the container 13. The pump 46 can be a liquid pump, such as a gear driven pump from Micropump Corporation.

A prism 16 is disposed over opening 15 to split the light beam into at least a first portion of the light beam 22 and a second portion of the light beam 20. This second portion of the light beam may also be referred to a reference beam. The prism can be placed over more than one opening and still used in this method. The prism 16 is typically glass or quartz, but the prism 16 material is not limited to these materials. Usable prisms 16 can be readily obtained from Edmonds Scientific and other high quality glass sources, including Corning Glass of Binghamton, N.Y. Although triangular shaped, ninety-degree glass prisms are depicted in the figures, other styles and shapes of prisms can be used. Additionally the prisms can be made of different optically clear materials, such as sapphire, and still used in these embodiments.

The prism 16 is preferably sealed over the opening 15 in a leak tight manner using a seal 38 or sealing material, such as an adhesive sealing material. The seal 38 can be an O-ring, such as elastomeric O-ring; or a gasket, such as EPDM or a terpolymer elastomers made from ethylene propylene diene-monomer or butyl amide gaskets. Alternatively, a clamp can be used to hold the prism 16 over the one or more openings.

A reference detector 30 and a measurement detector 26 are preferably placed beneath the prism 16 and the opening 15. By placing the detectors 26 and 30 beneath the prism 16 and opening 15, the chance of bubbles in the liquid interfering with the measurement detector 26 is reduced when the prism is inverted. The reference detector 30 measures the intensity of the reference beam 20. Known reference detectors are readily available and can be procured though Radio Shack.

The reference beam 20 is detected by reference detector 30 forming a reference signal 31. This reference signal 31 is used to compensate for the effects of temperature and for light source variations with regard to the intensity of the light source. As a further precaution, a housing (not shown) optionally can be used to completely enclose the entire system, including container, prism, and detectors. The housing can be used to protect the device from the elements or dirt in a printing house; or other problems, such as dripping water, which could dilute or otherwise affect the sample or the quality of reflected light to be measured.

Optional filters can be placed in the light path between the light source 10 and the measurement detectors 26 to remove unwanted wavelengths of light coming into contact with the detectors. It is also contemplated that polarizing filters may be employed as the amplitude of reflection from the prism-liquid interface is dependent on the polarization of the light.

The measurement detector 26 can be any known measurement detector for light. Preferably, the measurement detector 26 and the reference detector 30 have similar detection characteristics. More preferably, the measurement detector 26 and the reference detector 30 are the same type or model of detection device. Using a common type of detector helps to ensure that the output signals from the two detectors have similar response curves for the output signal (as a function of detected light and similar temperature and aging characteristics). Such lights sensors are available through many electronics supply companies.

At least a portion of the first portion of the light beam 22 passes through the opening 15 to the liquid and is reflected back from the liquid through the opening forming an attenuated beam 24. The measurement detector 26 is used to measure the intensity of the attenuated beam 24 to determine the light absorption level of the liquid, which is either the colorless liquid or the colored liquid with the known colorant value. The intensity of the attenuated beam 24 is related to the light absorption level of the liquid. The measurement detector 26 then produces a first liquid measurement signal 28. The measurement detector 26 can be a light sensor that produces a voltage, which can then be measured using a simple voltage measurement device such as a volt meter.

FIG. 2A depicts another example embodiment in which two liquids are used for measuring light absorption levels for a liquid for use in an ink jet printing system. The system for two liquids includes a second inlet 43 to allow the second liquid 14a to enter the container 13. The system has a second outlet 45 to allow the second liquid 14a to exit the container 13. The container 13 includes a second opening 52 that allows the divergent beam to be directed toward the second liquid 14a. Since two liquids are used, a second attenuated beam 25 and a second liquid measurement signal 29 are produced. A second measurement detector 27 is used to measure the intensity of the second attenuated beam and produce a second liquid measurement signal 29. Optional filters can be placed in front of the measurement detectors to remove unwanted wavelengths of light coming into contact with the detectors.

While the use of a reference beam 20, reference detector 30 and reference signal 31 help to provide a useful standard against which to compare the liquid measurement signal 28, they are not required. FIG. 2B depicts another example embodiment of the invention. In this embodiment, the container 13 has two fluid cavities, through which a fluid can pass through each. Liquid 14 passes through the container 13, entering through inlet 42 and leaving through outlet 44. A second fluid 14a also passes through the container 13, entering through port 43 and exiting through port 45. Fluid 14 makes contact with the prism 16 via opening 15 while fluid 14a makes contact with the prism 16 through opening 52.

The light source 10 produces light beam 12, which forms first portion of the light beam 22 upon entering the prism 16. A portion of the first portion of the light beam is reflected from the liquid-prism interface at opening 15 to form attenuated beam 24. The intensity of the attenuated beam 24 depends upon the absorptivity of liquid 14 at the wavelength of the light provided by light source 10. Measurement detector 26 produces a liquid measurement signal 28 in response to the intensity of the attenuated beam 24. Similarly, a portion of the first portion of the light beam 22 is reflected off the liquid-prism interface at opening 52 to produce a second attenuated beam 25. A second measurement detector 27 produces a second liquid measurement signal 29 in response to the intensity of the second attenuated beam 25.

In this embodiment, one of either the first of second liquid serves as a standard against which the measurement signal associated with the other liquid is compared. If the second fluid 14a is the reference liquid, device 34 is able to determine the concentration of fluid 14 by comparing liquid measurement signal 28 to the second liquid measurement signal 29 in conjunction with look-up table. 36. While shown including a single bounce reflected light path, the embodiments shown in FIGS. 2A and 2B can include a multiple bounce reflected light path like the one described with reference to FIGS. 4B and 5.

Figure 3A:
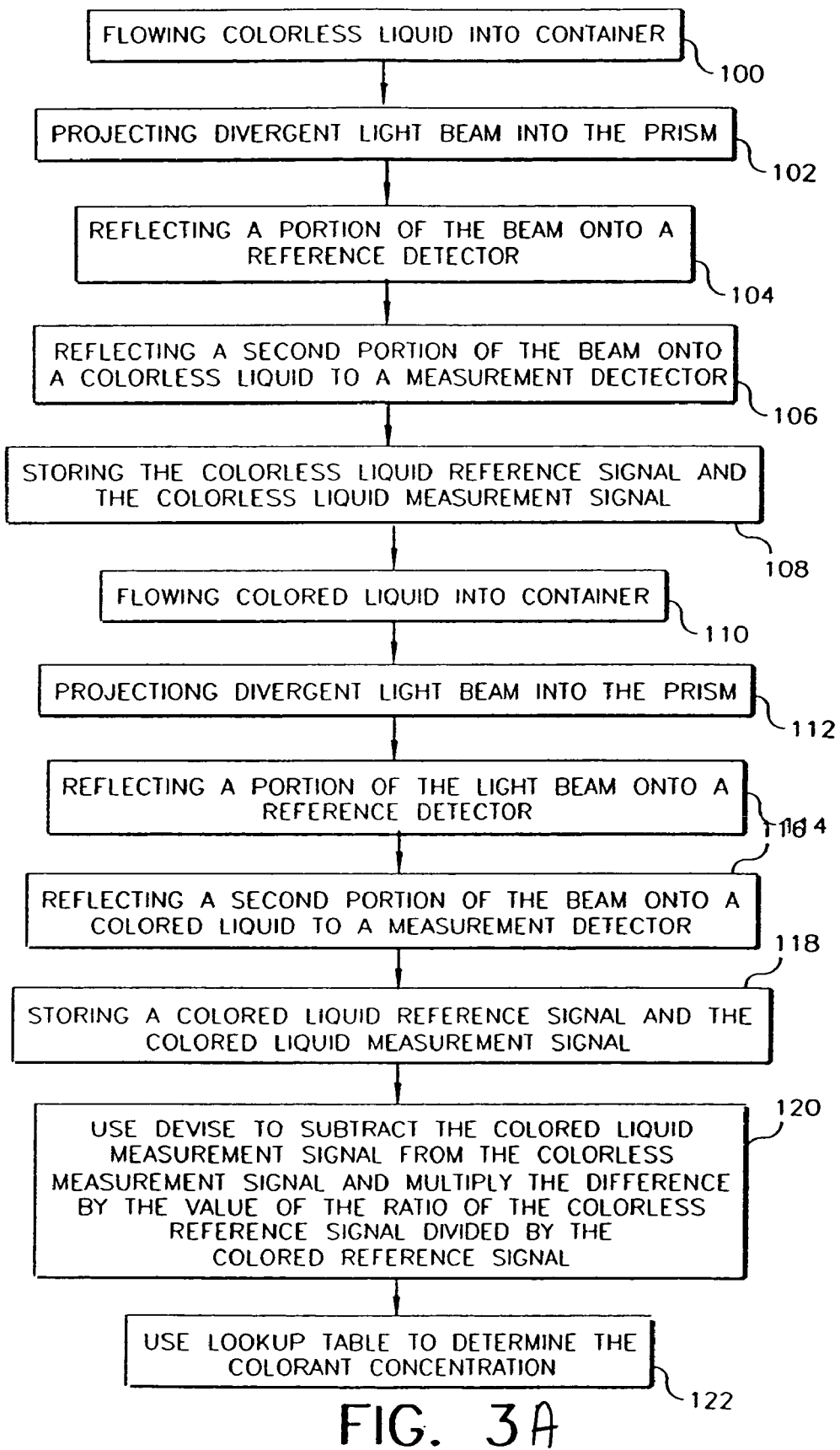
FIG. 3A depicts a block diagram of one of the methods of the example embodiments of the system.
Figure 3B:
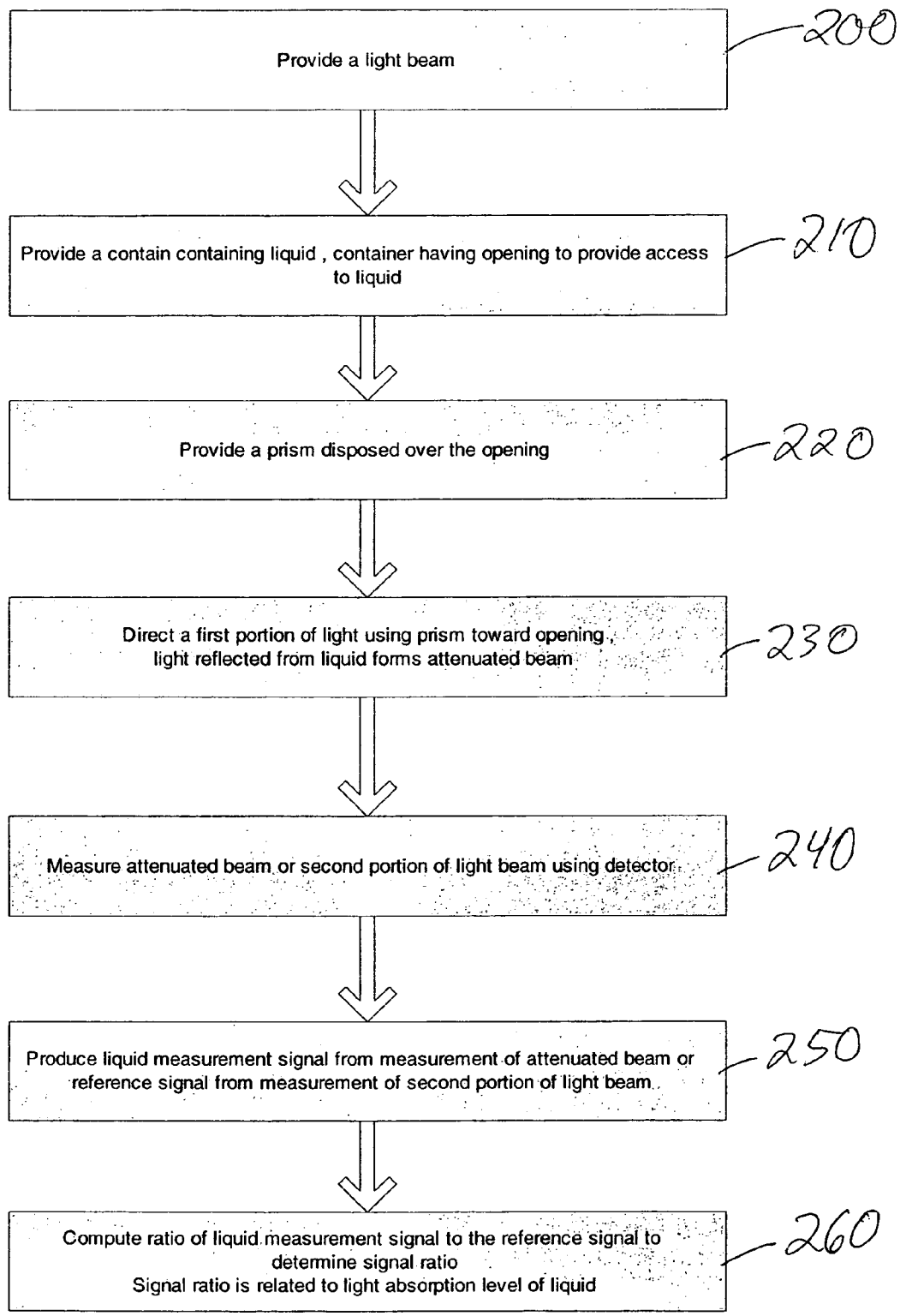
FIG. 3B depicts a block diagram of one of the methods of the example embodiments of the system.

FIGS. 3A and 3B are diagrams of example embodiments of a method for measuring light absorption levels of a liquid to control colorant concentration of the liquid for use in an ink jet printing system.

The methods involve measuring light absorption levels of a first liquid, such as a colorless liquid, and a second liquid, such as a colored liquid, to control colorant concentration of the colored liquid for use in a printing system. In an alternative embodiment, light absorption levels can be measured simultaneously for a colorless liquid and a colored liquid. In another embodiment, two colored liquids can be measured simultaneously. The printing system is typically an ink jet printing system.

The embodied methods entail flowing colorless liquid into a container 13 with an opening and a prism disposed over the opening (Step 100). Preferably, the prism is oriented so that air bubbles do not interfere with the first portion of the light beam. In the alternative embodiment mentioned above, a first liquid flows into a first channel of the container having a first opening and a second liquid flows into a second channel of the container having a second opening. The first and second fluids flow into the respective channels simultaneously for this embodiment. For the two channel embodiment, both openings have the same prism disposed over the openings.

The methods continue by projecting a divergent light beam from a light source onto the prism (Step 102) and reflecting a first portion of the divergent beam from the prism to a reference detector to measure intensity of the divergent beam and obtain a reference signal (Step 104).

A second portion of the divergent beam is passed through the prism onto the opening onto the colorless liquid. Light reflects from the fluid forming a light beam that is focused by the opening forming an attenuated beam. The attenuated beam is measured by a measurement detector (Step 106). The measurement detector provides a colorless liquid measurement signal.

Alternatively, two portions of the divergent beam can pass through the prism and through both the first and second openings. The light passing through the first opening reflects onto the first liquid and the light passing through the second opening reflects onto the second liquid, which is typically a liquid of known colorant concentration. The light reflects back through both openings, and is focused by the openings, forming two attenuated beams. Each beam passes to a measurement detector to obtain a first and a second liquid measurement signals. The reference and liquid measurement signals can be stored for later use (Step 108).

Colored liquid then flows into the container (Step 110). Divergent light beam is projected into the prism (Step 112). The first portion of the divergent beam is reflected from the prism to a reference detector to measure intensity of the divergent beam and obtain a reference signal (Step 114).

A second portion of the divergent beam is passed through the prism onto an opening onto the colored liquid. A focused light beam is reflected from the colored liquid to a measurement detector (Step 116). The opening acts as a focusing lens to focus the light. The measurement detector provides a colored liquid measurement signal.

The method ends by computing simple mathematical equations from the measured signals (Step 120) to determine the colorant concentration of the liquid by comparing its light adsorption value to those of liquids of known colorant concentration. The mathematical equations are computed using a device 34, such a microprocessor, a computer, or circuitry that enables simple mathematical calculations to occur.

A look-up table (Step 122) can be used. The look-up table is used to find light absorption values of the measured liquid to determine the concentration of the colorant in the measured liquid. Signal ratio/colorant concentration factors can be used to calculate the concentration of the colorant in the liquid. The signal ratio/colorant concentration factor can be derived from measurements with the system using a colorless liquid, a liquid with a known colorant concentration, or a toner with a known colorant concentration.

Referring to FIG. 3B, the method of measuring light absorption levels for a liquid for use in a ink jet printing system begins with providing a light beam using a light source (Step 200). A container is provided to receive a liquid. The container includes an opening to provide access to the liquid (Step 210). The liquid includes a light absorption level. A prism is disposed over the opening (Step 220). At least a first portion of the light beam is directed using the prism toward the opening to the liquid such that the at least a portion of the first portion of the light beam is reflected back from the liquid forming an attenuated beam (Step 230). At least one of at least a portion of the attenuated beam and a second portion of the light beam is measured using a detector (Step 240). At least one of a liquid measurement signal that is related to the light absorption level of the liquid from the portion of the attenuated beam and a reference signal from the second portion of the light beam are produced using the detector (Step 250). A ratio of the liquid measurement signal to the reference signal is computed to determine a signal ratio. The signal ratio is related to the light absorption level of the liquid (Step 260). A concentration of colorant in the liquid can be determined using one of a look-up table for comparing the signal ratio to the look-up table to obtain the concentration of colorant in the liquid and a signal ratio/colorant concentration factor to calculate the concentration of colorant in the liquid.

Figure 4A:
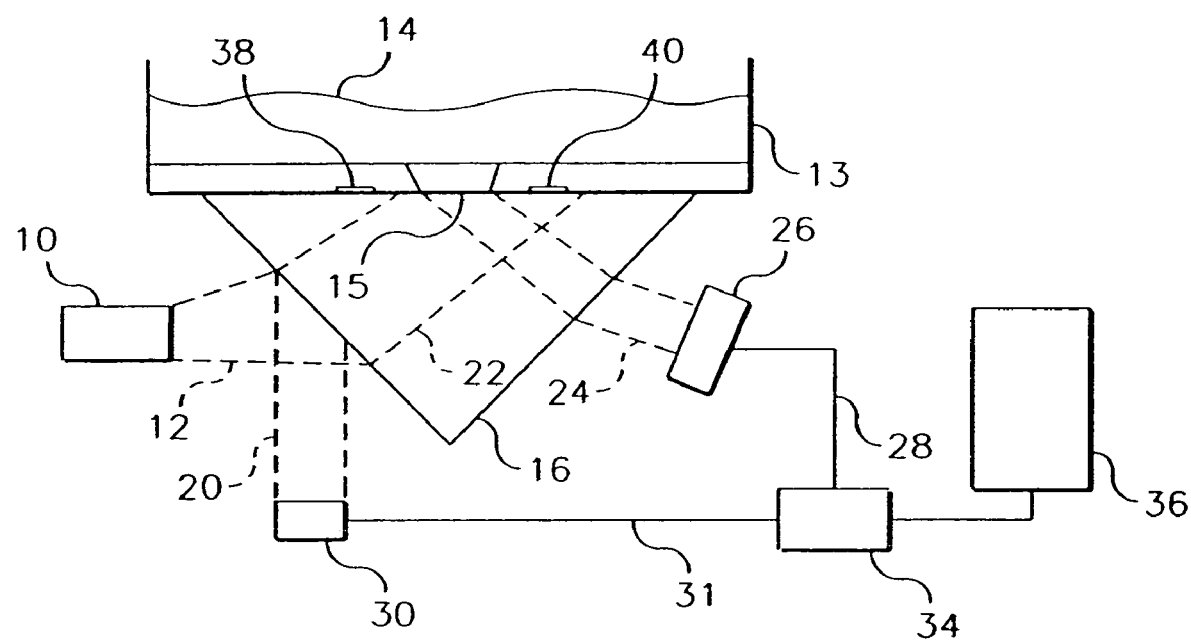
FIG. 4A depicts a schematic cross sectional view of another example embodiment of the system when used as, for example, a batch measurement system.

The example embodiments of the system can be used for a steady state flow of liquid through the container or can be used for a batch process. For example, FIG. 4A depicts an embodiment of the system that can be used for the batch process. The batch system is similar to the steady-state system, but the container 13 holds a static, non-flowing volume of liquid 14.

Figure 4B:
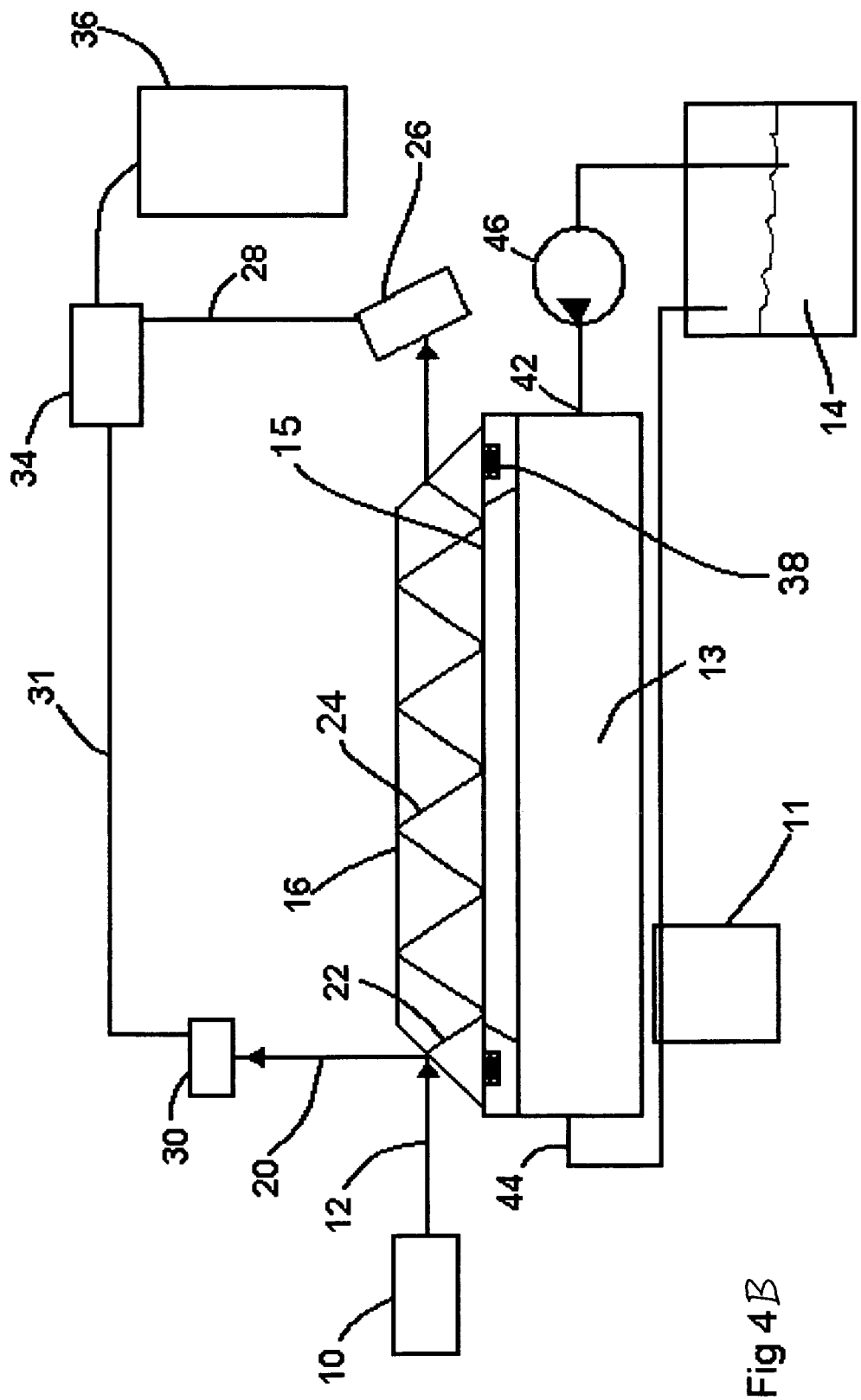
FIG. 4B depicts a schematic cross sectional view of another example embodiment of the system.

FIG. 4B depicts another example embodiment of the invention. Similar to the embodiment depicted in FIG. 1, the embodiment shown in FIG. 4B has a light source 10 producing a light beam 12, which is directed toward the prism 16. A portion of the light beam 12 is reflected at the surface of the prism 16, forming reference beam 20. The reference beam 20 is detected by reference detector 30, which produces a reference signal 31. The reference signal level is dependent on the intensity of the light detected by the reference detector. The light that enters the prism forms the first portion of the light beam 26.

The container 13 has an opening 15 which allows the liquid 14 to make contact with the prism. The first portion of the light beam 22 strikes the liquid-prism interface. The light beam is reflected at the liquid-prism interface to form an attenuated light beam 24. The attenuated beam 24 is repeatedly reflected from the liquid-prism interface and from the prism face opposite the liquid-prism interface, until it emerges from the end of the prism. The attenuated beam is further attenuated with each reflection off the liquid-prism interface. The reflection angle of the attenuated beam at the air-prism interface can be such that there is total internal reflection of the attenuated beam at this interface. When this is the case, there is no attenuation of the light at each reflection from air-prism interface. Therefore assuming the amplitude of the reflected light, $I_{refl}$ is $R_{amp}$ times the amplitude of the incident light $I_{in}$, that is $I_{refl} = R_{amp} * I_{in}$, the intensity of the light after n reflections from the liquid-prism interface is given by: $I_{out} = I_{in} * (Ramp)^n$.

This multiple bounce light path configuration can therefore greatly increase the sensitivity of the detector for weakly absorbing liquids when compared to other types of systems known in the art.

Figure 5:
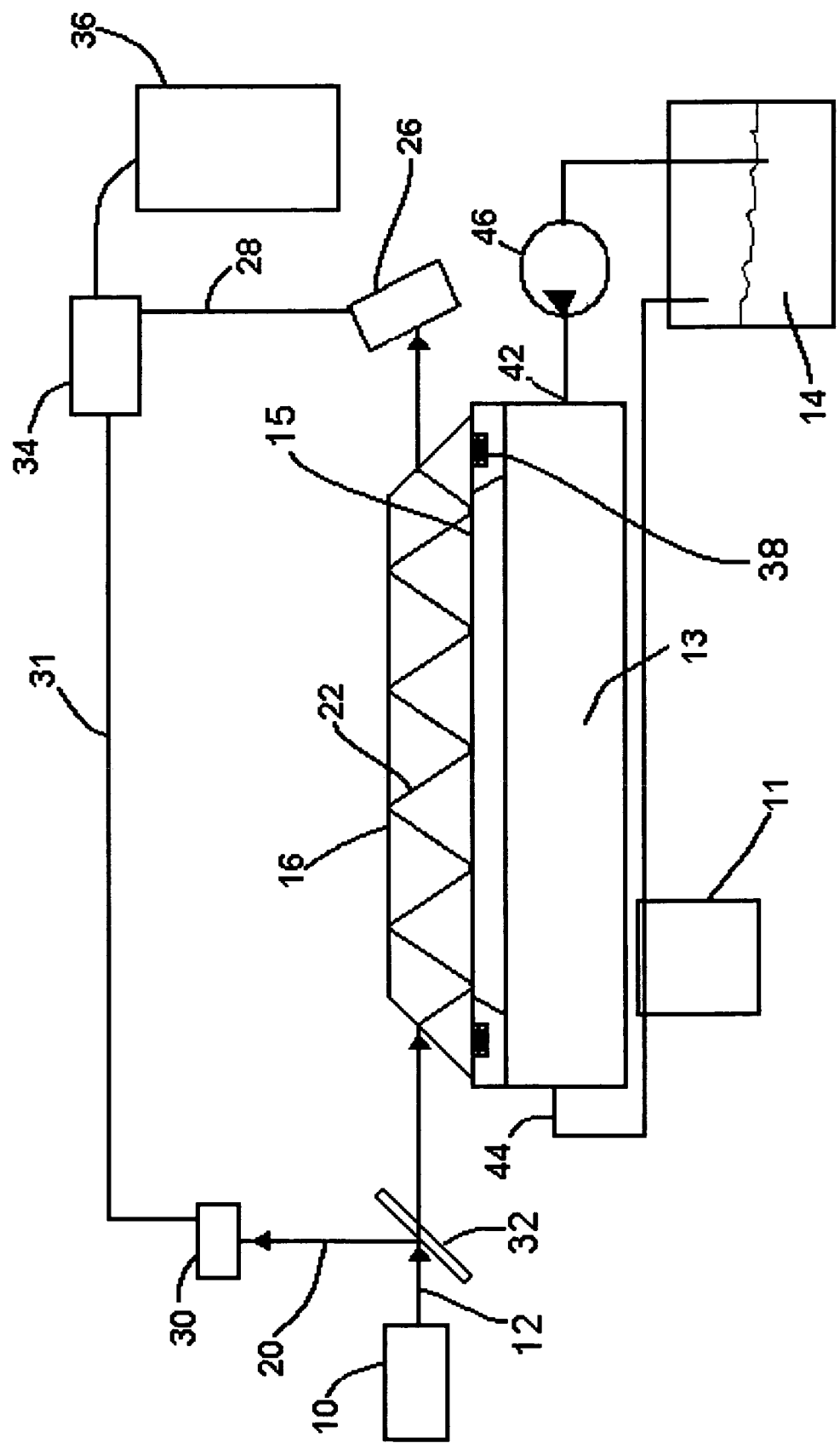
FIG. 5 depicts a schematic cross sectional view of another example embodiment of the system.

While the embodiments shown in FIGS. 1 and 4 produce a reference beam from light reflected off the surface of the prism, it is not required. For example, in the embodiment shown in FIG. 5, a beam splitter 32 is used to create the reference beam 20. The other elements of the embodiment shown in FIG. 5 are the same as those elements of the embodiment shown in FIG. 4.

Figure 6:
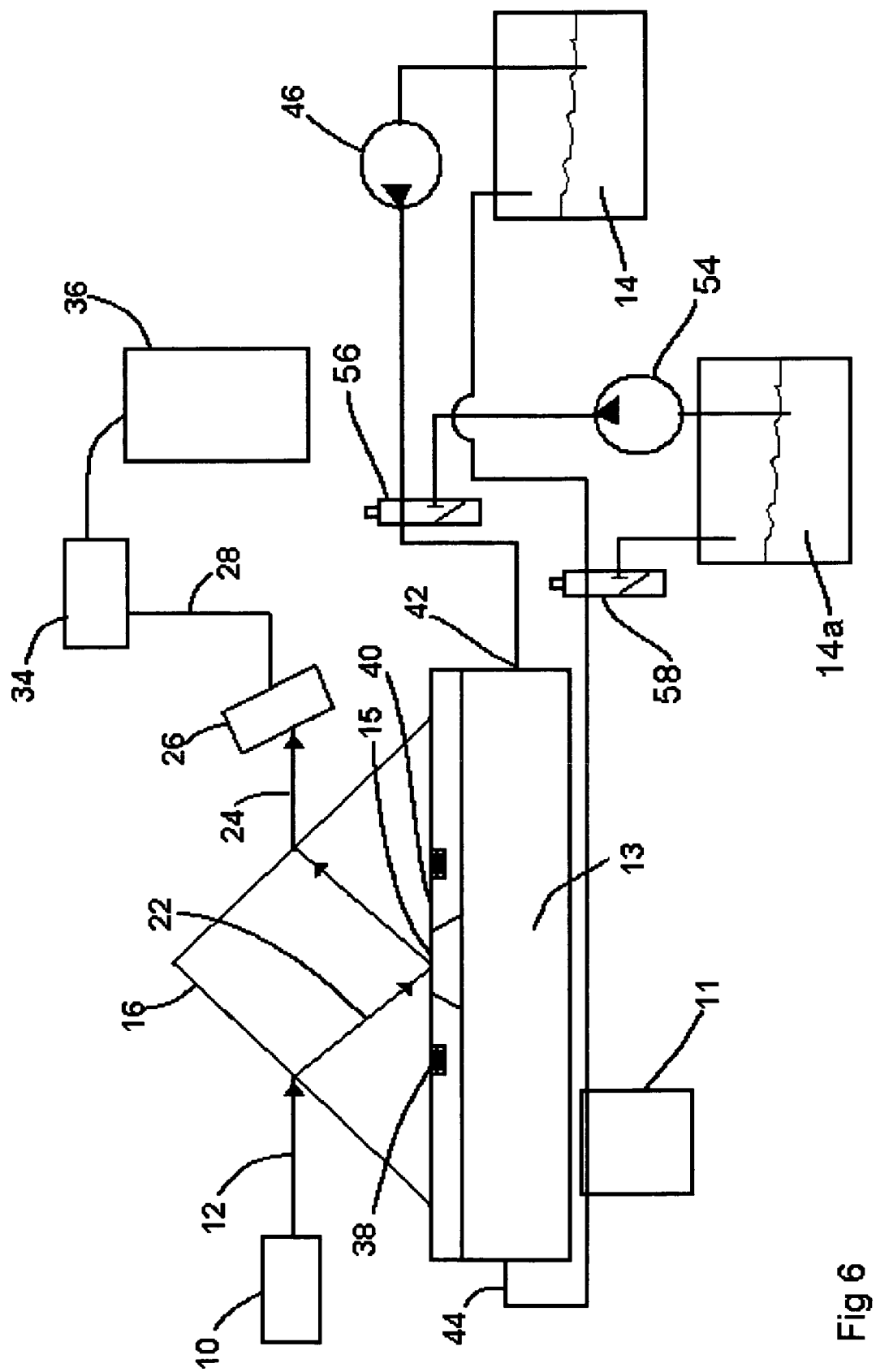
FIG. 6 depicts a schematic cross sectional view of another example embodiment of the system.

FIG. 6 depicts another example embodiment of the present invention. In this embodiment, there is neither a reference beam nor a second attenuated beam or their associated detectors. In this embodiment, the first fluid 14 and second fluid 14a are tested sequentially. For example, pump 54 and valves 56 and 58 act to allow fluid 14a to be circulated through the container 13. With fluid 14a in contact with the prism, a liquid measurement signal 28a, which is related to the absorptivity of liquid 14a, is produced. The liquid measurement signal 28a is then saved in device 34. Once this measurement is complete, pump 54 is turned off, pump 46 is turned on, and valves 56 and 58 are activated to enable liquid 14 to pass through the container 13. With liquid 14 in contact with the prism, a liquid measurement signal 28, which is related to the absorptivity of liquid 14, is produced. The concentration of liquid 14 may then be determined by device 34 by comparing the liquid measurement signal 28 with the previously determined second liquid measurement signal 28a in conjunction with the look-up table 36. While shown including a single bounce reflected light path, the embodiment shown in FIG. 6 can include a multiple bounce reflected light path like the one described with reference to FIGS. 4B and 5.

The embodiments have been described in detail with particular reference to certain preferred embodiments thereof, but it will be understood that variations and modifications can be effected within the scope of the embodiments, especially to those skilled in the art.

PARTS LIST 10 light source
11 printing system
12 divergent light beam
13 container
14 first liquid
14 second liquid
15 opening
16 prism
20 reference beam
22 first portion of the light beam
24 attenuated beam
25 second attenuated beam
26 measurement detector
27 second measurement detector
28 liquid measurement signal
29 second liquid measurement signal
30 reference detector
31 reference signal
34 device
36 look-up table
38 seal
40 non reflective coating
42 inlet
43 second inlet
44 outlet
45 second outlet
46 pump
52 second opening
100 Step—flowing colorless liquid into container
102 Step—projecting divergent light beam into prism
104 Step—reflecting a portion of the beam onto a reference detector
106 Step—reflecting a second portion of the beam onto a colorless liquid to a measurement detector
108 Step—storing the colorless liquid reference signal and the colorless liquid measurement signal
110 Step—flowing colored liquid into container
112 Step—projecting divergent light beam into the prism
114 Step—projecting divergent light beam onto a reference detector
116 Step—reflecting a second portion of the beam onto a colorless liquid to a measurement detector
118 Step—storing a colored liquid reference signal and the colored liquid reference measurement signal
120 Step—using a device to calculate the value
122 Step—using a lookup table to determine the colorant concentration
200 Step—providing a light beam
210 Step—providing a container including an opening
220 Step—disposing a prism over the opening
230 Step—forming an attenuated beam
240 Step—measuring
250 Step—producing at least one of a measurement and reference signal
260 Step—computing a ratio

The invention claimed is:

1. A system for measuring light absorption levels for a liquid for use in a ink jet printing system, the system comprising:
    a light source operable to provide a light beam;
    a container adapted to receive a liquid, the container including an opening to provide access to the liquid, the liquid including a light absorption level;
    a prism disposed over the opening, the prism being operable to direct at least a first portion of the light beam toward the opening to the liquid such that the at least a portion of the first portion of the light beam is reflected back from the liquid forming an attenuated beam;
    a detector operable to measure at least one of at least a portion of the attenuated beam and a second portion of the light beam, the detector being operable to produce at least one of a liquid measurement signal that is related to the light absorption level of the liquid from the portion of the attenuated beam and a reference signal from the second portion of the light beam; and
    a device operable to compute a ratio of the liquid measurement signal to the reference signal to determine a signal ratio, wherein the signal ratio is related to the light absorption level of the liquid.

2. The system of claim 1, further comprising one of a look-up table for comparing the signal ratio to the look-up table to obtain a concentration of colorant in the liquid and a signal ratio/colorant concentration factor to calculate the concentration of the colorant in the liquid.

3. The system of claim 1, wherein the light source is one of a laser diode, a light bulb, a light emitting diode, a tungsten filament, and a light source operable to produce polarized light.

4. The system of claim 1, the opening being a first opening, the container comprising:
    a first channel associated with the first opening, the channel being adapted to receive the liquid;
    a second opening; and
    a second channel associated with the second opening, the second channel being adapted to receive a fluid, wherein the prism is disposed over the first and second openings and is operable to direct the at least first portion of the light beam toward the first and second openings.

5. The system of claim 1, wherein the prism is one of a quartz prism and a glass prism.

6. The system of claim 1, wherein the prism is shaped and the opening is sized such that the at least a portion of the attenuated beam is measured by the detector and is reflected back from the liquid at least two times.

7. The system of claim 1, wherein the second portion of the light beam is created by at least one of reflection from a face of the prism, a beam splitter positioned between the light source and the prism, and divergence of the light beam.

8. The system of claim 1, wherein the detector comprises:
a first detector operable to measure the portion of the attenuated beam, the first detector being operable to produce the liquid measurement signal that is related to the light absorption level of the liquid from the portion of the attenuated beam; and
a second detector operable to measure the second portion of the light beam, The second detector being operable to produce the reference signal from the second portion of the light beam.

9. The system of claim 1, wherein the detector compnses:
a single detector adapted to alternately measure the portion of the attenuated beam and the second portion of the light beam.

10. The system of claim 9, the liquid being a first liquid, wherein the second portion of the light beam includes light reflected back from a second liquid.

11. A method of measuring light absorption levels for a liquid for use in a ink jet printing system, the method comprising:
providing a light beam using a light source;
providing a container adapted to receive a liquid, the container including an opening to provide access to the liquid, the liquid including a light absorption level;
providing a prism disposed over the opening;
directing at least a first portion of the light beam using the prism toward the opening to the liquid such that the at least a portion of the first portion of the light beam is reflected back from the liquid forming an attenuated beam;
measuring at least one of at least a portion of the attenuated beam and a second portion of the light beam using a detector;
producing at least one of a liquid measurement signal that is related to the light absorption level of the liquid from the portion of the attenuated beam and a reference signal from the second portion of the light beam using the detector; and
computing a ratio of the liquid measurement signal to the reference signal to determine a signal ratio, wherein the signal ratio is related to the light absorption level of the liquid.

12. The method of claim 11, further comprising determining a concentration of colorant in the liquid using one of a look-up table for comparing the signal ratio to the rook-up table to obtain the concentration of colorant in the liquid and a signal ratio/colorant concentration factor to calculate the concentration of colorant in the liquid.

13. The method of claim 11, wherein directing at least a first portion of the light beam using the prism toward the opening to the liquid such that the at least a portion of the first portion of the attenuated beam indudes causing the portion of the attenuated beam to be reflected back from the liquid at least two times.

14. The method of claim 11, wherein measuring the second portion of the light beam includes creating the second portion of the light beam by causing the light beam to reflect from one of a face of the prism and beam splitter positioned between the light source and the prism.

15. The method of claim 11, wherein measuring the second portion of the light beam includes creating the second portion of the light beam by causing the light beam to diverge.

16. The method of claim 11, wherein measuring at least one of the portion of the attenuated beam and the second portion of the light beam includes alternately measuring the portion of the attenuated beam and the second portion of the light beam.

17. The method of claim 16, the liquid being a first liquid, wherein alternately measuring the first portion of the attenuated beam and the second portion of the light beam includes reflecting light back from a second liquid thereby creating the second portion of the light beam.

* * * * *

UNITED STATES PATENT AND TRADEMARK OFFICE
CERTIFICATE OF CORRECTION

PATENT NO. : 7,593,107 B2
APPLICATION NO. : 11/395785
DATED : September 22, 2009
INVENTOR(S) : James D. Wolf et al.

It is certified that error appears in the above-identified patent and that said Letters Patent is hereby corrected as shown below:

| | |
|---|---|
| Column 13, line 8 | In Claim 8, delete "The" and insert -- the --, therefor. |
| Column 13, line 11 | In Claim 9, delete "compnses:" and insert -- comprises: --, therefor. |
| Column 14, line 7 (approx.) | In Claim 12, delete "rook-up" and insert -- look-up --, therefor. |
| Column 14, line 15 | In Claim 13, delete "indudes" and insert -- includes --, therefor. |

Signed and Sealed this

Thirteenth Day of April, 2010

David J. Kappos
*Director of the United States Patent and Trademark Office*